United States Patent [19]
Haber et al.

[11] Patent Number: 5,558,874
[45] Date of Patent: Sep. 24, 1996

[54] MULTI-COMPARTMENT APPLICATOR FOR PACKAGING, RECONSTITUTING AND APPLYING A DEHYDRATED MULTI-CONSTITUENT MEDICATION

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 354,219

[22] Filed: Dec. 12, 1994

[51] Int. Cl.$^6$ ............................................. A61K 9/00
[52] U.S. Cl. ................. 424/402; 424/401; 514/844; 514/848; 514/859; 401/132; 401/196
[58] Field of Search ..................... 424/401, 402; 514/844, 846, 848, 859

[56] References Cited

U.S. PATENT DOCUMENTS

| | | | |
|---|---|---|---|
| 4,140,409 | 2/1979 | DeVries | 401/132 |
| 4,812,067 | 3/1989 | Brown et al. | 401/132 |

*Primary Examiner*—Thurman K. Page
*Assistant Examiner*—Sharon Howard
*Attorney, Agent, or Firm*—Hawes & Fischer

[57] ABSTRACT

A compact single use applicator is disclosed having a dry medication (e.g, a dehydrated or lyophilized astringent disinfectant that is adapted to treat ache and has been reduced to a powder) stored in a flexible mixing chamber. Liquid diluents are stored in first and second flexible chambers. Fluid communication between the diluents in the first and second chambers and the dry medication in the mixing chamber is blocked by normally closed, pressure activated fluid paths. By compressing the first and second chambers, corresponding hydraulic pressures are generated in the diluents thereof which force open the pressure activated paths. Accordingly, the diluents in the first and second chambers are introduced under pressure to the dry medication in the mixing chamber to rehydrate and reactivate the medication. The reconstituted multi-constituent liquid medication is then supplied from the mixing chamber to a dispensing chamber via another normally closed pressure activated fluid path. The liquid medication is absorbed by an applicator pad, or the like, that is surrounded by the dispensing chamber, whereby the medication can be applied via an opening through the dispensing chamber to a relatively wide tissue area as a topical treatment for ache or other skin disorder.

20 Claims, 8 Drawing Sheets fig. 1 fig. 2 fig.3 fig.4 fig.5 fig.6 fig.7 fig.8 fig. 9 fig. 13 fig. 14 fig. 15 fig. 16

MULTI-COMPARTMENT APPLICATOR FOR PACKAGING, RECONSTITUTING AND APPLYING A DEHYDRATED MULTI-CONSTITUENT MEDICATION

BACKGROUND OF THE INVENTION

1. Field of the Invention

This invention relates to a compact, single use applicator in which a lyophilized pharmaceutical is packaged in powder form to be rehydrated prior to use by the addition thereto of liquid diluents stored in respective sealed compartments so that a precise amount of reconstituted medication can be applied from an absorbent pad, or the like, directly to a target site for the treatment of acne, and other skin disorders.

2. Background Art

It is sometimes desirable for those suffering from acne or other skin disorders to periodically apply a topical medication to a tissue area to enhance treatment and speed healing. It is common to package the topical acne medication as a liquid or cream in a bottle or tube or as a series of moist pads in a jar. Because the liquid, cream and moisture is subject to evaporation and/or deterioration with time, the shelf life of the usual packaged medication may be undesirably shortened. That is to say, once the container is opened and the medication is exposed to the atmosphere, some of the moist treatment pads may dry out while some of the liquid or cream medication may evaporate or spill or lose its effectiveness.

In addition, it may not be convenient to carry on one's person a relatively large container in which the liquid medication or moist pads are packaged. More particularly, the user may have to transport a bottle, tube or jar even though only a small portion of the medication therein will be used during any given treatment. Moreover, there is no readily available way for the user to control the application of a precise amount of acne medication to this tissue. Too much or too little liquid or cream is sometimes dispensed from a bottle or tube. For example, if the tissue area to be treated is small, a moist pad is often saturated with more medication than that actually needed to adequately treat the acne.

In this same regard, some topical treatments require that two or more liquids and/or solids be mixed together to activate the acne medication. However, the liquids and/or solids can not be mixed prior to shipment by the manufacturer, because the resultant medication may lose its effectiveness, particularly if the medication will be shelved for a long time. Hence, it has been a long standing problem to provide a multi-constituent acne medication in a compact package where the different constituents are isolated from one another but may be conveniently and selectively mixed together in a sterile environment just prior to use so that the medication may be applied directly from the package to the tissue area undergoing treatment.

The foregoing problems result in inefficiency and/or waste which can prove to be inconvenient, particularly if the medication is expensive or the acne requires a long period of treatment. In some cases, the user may have to replace the medication prematurely, because of the evaporation, deterioration or inefficient use thereof. In other cases, the user may elect to forego treatment altogether, especially when travelling far from home.

Reference may be made to our earlier U.S. Patent application Ser. No. 08/302,587 filed September, 1994 for an example of an applicator for a multi-constituent medication to treat skin disorders, such as acne.

SUMMARY OF THE INVENTION

In general terms, a compact, low profile and single use pad applicator is disclosed in which a dehydrated multi-constituent medication is packaged and ready to be activated for direct application to a target site. According to the preferred embodiment of the invention, the applicator includes a generally planar body having a pair of closed bubble-shaped chambers located side-by-side one another at the proximal end of the body and a closed bubble-shaped chamber located at the middle of the body. Another chamber having an opening through the top thereof is located at the distal end of the body. The body and the proximal, middle and distal chambers are all preferably manufactured from a flexible and optically transparent, gas and liquid impermeable material that is capable of being thermally bonded or sonically welded. A pair of normally closed (i.e. sealed), pressure activated valves lie between the middle chamber and respective ones of the proximal chambers. Another normally closed, pressure activated value lies between the distal chamber to the middle chamber.

In the packaged, ready-to-activate applicator configuration, a liquid diluent is stored in each of the proximal chambers. A pharmaceutical is stored in the middle chamber. The pharmaceutical is preferably a dehydrated topical astringent disinfectant that is known to treat acne and that has been reduced to powder by a conventional lyophilization process. An applicator pad formed from an absorbent material is bonded to the top face of the applicator body and surrounded by the distal chamber. A removable cover having a pull tab extending therefrom extends over top the distal chamber so as to close the opening therethrough and seal the pad applicator in a sterile environment therewithin. A relatively rigid (e.g. thin cardboard) backing is bonded to the bottom face of the applicator body below the proximal and middle chambers at the top face of the body. A fold line extends laterally across the backing so as to divide the backing into a proximal end lying underneath the proximal chambers and a distal end lying underneath the middle chamber.

To activate and use the pad applicator, the user first squeezes the bubble-shaped proximal chambers so as to apply compressive forces thereagainst and generate corresponding hydraulic pressures within the diluents thereof. The hydraulic pressure of the diluents ruptures (i.e. breaks) the seals of the normally closed, pressure-activated values between the proximal chambers and the middle chamber to permit the diluents to be expulsed under pressure from the proximal chambers and introduced to and mixed with the powder pharmaceutical stored in the middle chamber. Accordingly, the dry astringent disinfectant of the pharmaceutical powder is rehydrated to form a liquid medication. The liquid medication may be relocated back and forth between the middle and proximal chambers to insure that the entire volume of the diluents has been mixed with the powder pharmaceutical.

Next, the user bends the backing around the fold line to rotate the proximal end of the backing and the proximal end of the applicator body towards the distal end of the backing and the middle of the body until the proximal and middle chambers are arranged face-to-face one another. By squeezing on the opposing ends of the backing, the user applies a compressive force against the middle chamber to generate a corresponding hydraulic pressure within the rehydrated liquid medication therein so as to rupture and open the seal made by the normally closed, pressure-activated valve between the middle and distal chambers. Accordingly, the rehydrated liquid medication is expulsed from the middle chamber and supplied, under pressure, to the distal chamber where it is absorbed by the applicator pad. Then, the user grasps the pull tab and separates the removable cover from the applicator to permit access via the opening in the distal chamber to the applicator pad that has been saturated with reconstituted medication. Finally, the user moves the saturated pad into contact with the tissue to be treated so that the rehydrated liquid medication can be applied directly from the applicator to the target site. When the topical treatment has been completed, the spent applicator is simply and conveniently discarded.

DETAILED DESCRIPTION

Figure 1:
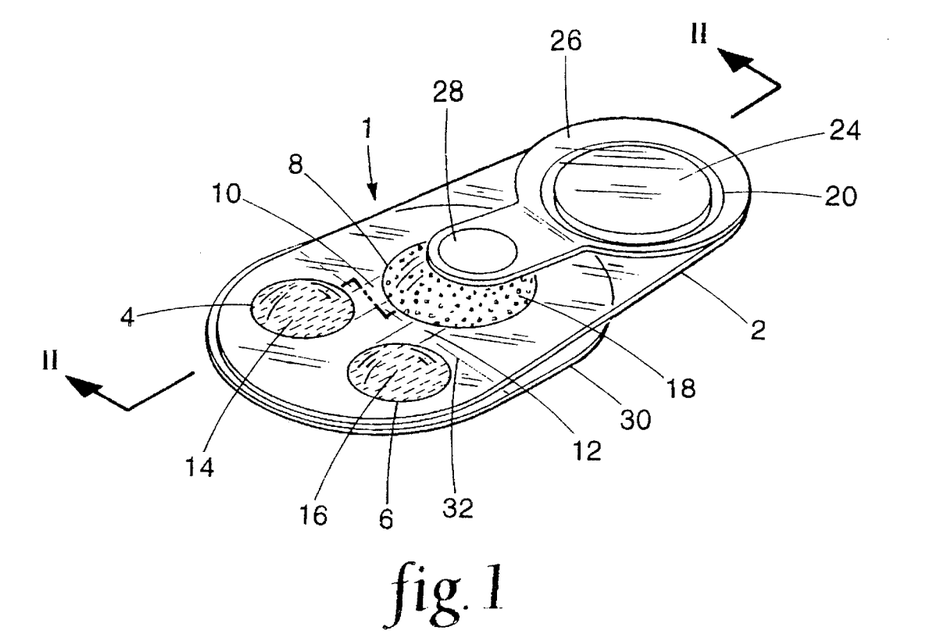
FIG. 1 is a perspective view of a multi-compartment pad applicator for packaging, reconstituting and applying a dehydrated multi-constituent medication and which forms the present invention.
Figure 2:
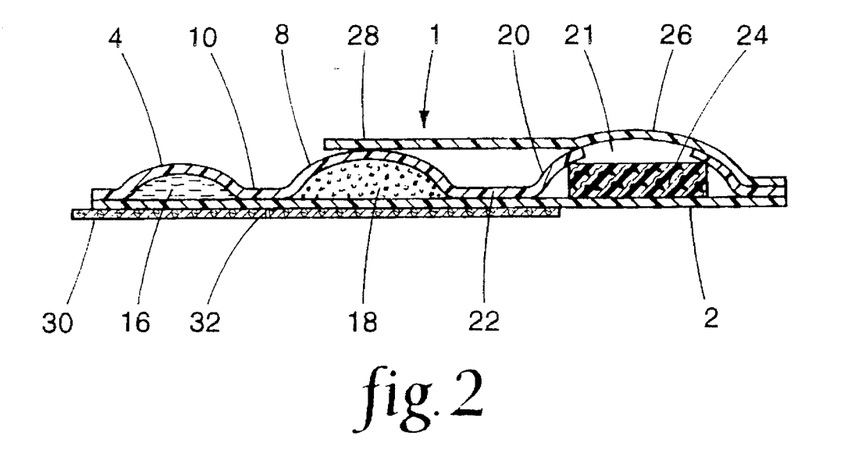
FIG. 2 is a cross-section of the pad applicator taken along lines 2—2 of FIG. 1.

FIGS. 1 and 2 of the drawings illustrate a compact and low profile, single use pad applicator 1 in which a topical acne medication is packaged for application by a user directly to a targeted tissue site for the treatment of acne or other skin disorders. By virtue of the foregoing, a precise amount of acne medication may be applied to a relatively wide tissue area requiring treatment. The applicator 1 includes a planar body 2. A pair of bubble-shaped chambers 4 and 6 are arranged in spaced side-by-side alignment with one another near the proximal end of the body 2, and a single bubble-shaped mixing chamber 8 is located at approximately the middle of the body 2.

The body 2, each of the proximal chambers 4 and 6, and the middle chamber 8 of pad applicator 1 are preferably manufactured from a gas and liquid impermeable, heat-sealable material that is suitable for thermal bonding or sonic welding. This material should be both flexible and optically so that, as will be explained in greater detail hereinafter, the user will be able to manually manipulate the chambers 4, 6 and 8 and visualize mixing the contents thereof. By way of example, a material that is suitable to manufacture the pad applicator 1 of this invention is a commercially available Mylar-polyethylene barrier layer material. To this end, the proximal chambers 4 and 6 and the middle chamber 8 are sealed against the top face of body 2 to form air and liquid-tight closures at the interface therewith.

In the packaged, ready-to-activate applicator configuration 1 of FIGS. 1 and 2, the middle chamber 8 is fluidically isolated from each of the proximal chambers 4 and 6 by means of respective normally closed valves 10 and 12. Valve 10 is a relatively narrow fluid orifice that is integrally formed with and extends between one of the proximal chamber 4 and the middle chamber 8. Similarly, valve 12 is a relatively narrow fluid orifice that is integrally formed with and extends between the other proximal chamber 6 and the middle chamber 8. As is best shown in FIG. 2, each valve 10 and 12 is, in the packaged condition of applicator 1, sealed and closed against the body 2 to prevent communication between the proximal chambers 4 and 6 and the middle chamber 8, and vice versa.

In the packaged, ready-to-activate applicator configuration 1, liquid diluents 14 and 16 are stored in each of the bubble-shaped proximal chambers 4 and 6. By way of example only, the diluent 14 stored in proximal chamber 4 is 20 grams of 5% Benzylperoxide gel. By way of further example, the diluent 16 stored in proximal chamber 6 is 3 milliliters of ethyl alcohol. However, the diluents 14 and 16 stored in chambers 4 and 6 may also be identical to one another so that the volume of diluent available to activate the acne medication to be applied to the targeted tissue area may be selectively controlled by the user.

Sealed within the middle chamber 8 is a pharmaceutical. The pharmaceutical is preferably a dehydrated topical astringent disinfectant that is known for treating acne and that has been reduced to a powder 18 by means of a conventional lyophilization process. By way of example, the pharmaceutical in middle chamber 8 may be 800 milligrams of erythromycin powder 18. However, it is to be expressly understood that the pharmaceutical in chamber 8 could also take the form of a gel or a dry medication wafer, rather than a powder. As will soon be disclosed, the liquid diluents 14 and 16 of proximal chambers 4 and 6 will be introduced to and mixed with each other and with the dehydrated disinfectant 18 in middle chamber 8 in order to rehydrate and activate the medication when the user is ready to treat his acne.

Located near the distal end of the body 2 of applicator 1 is a partially open chamber 20 that is formed from the same material used to manufacture the body 2 and the bubble-shaped chambers 4, 6 and 8. The distal chamber 20 communicates with the middle chamber 8 by way of a valve 22 (best shown in FIG. 2) which is similar to the earlier disclosed valves 10 and 12. Therefore, in the packaged configuration of applicator 1, valve 22 is a relatively narrow fluid orifice that is sealed and closed against the body 2 to prevent communication between the middle and distal chambers 8 and 20.

Located within the partially open distal chamber of applicator 1 is a sterile applicator pad 24. The applicator pad 24 is formed from an absorbent material, such as sponge, cotton, or the like. The bottom side of pad 24 is adhesively bonded to the body 2. The top side of pad 24 is surrounded by the partially open distal chamber 20 and accessible via an opening 21 therethrough. However, to preserve the sterility of the pad 24 in the packaged, ready-to-activate configuration of the applicator 1, the opening 21 through the distal chamber 20 is sealed by a removable cover 26 that may be formed from the same transparent, gas and liquid impermeable material that is used to manufacture the body 2 and chambers 4, 6 and 20 of applicator 1.

More particularly, the removable cover 26 is adhesively bonded to the distal chamber 20 so as to extend across and thereby close the opening 21 thereof with the absorbent applicator pad 24 spaced therebelow. A relatively narrow pull tab 28 projects proximally from the cover 26 to a manually accessible location (e.g. atop middle chamber 8). As will soon be described, the user may remove the cover 26 from the distal chamber 20 to gain access to the applicator pad 24 by way of opening 21 by grasping the pull tab 28 and exerting a distal pulling force thereon to break the adhesive bond between the cover 26 and the distal chamber 20.

A backing 30 is adhesively bonded to the bottom face of the body 2 of applicator 1. The backing 30 is formed from a relatively rigid material, such as thin cardboard, plastic or the like. For a reason which will soon become apparent, the backing 30 is bonded to the body 2 so as to lie below the proximal and middle bubble-shaped chambers 4, 6 and 8. A fold line 32 (best shown in FIG. 1) runs laterally across the backing 30 at a location between the proximal chambers 4 and 6 and the middle chamber 8 so as to divide the backing 30 into proximal and distal ends. As will soon be disclosed, the backing 30 is adapted to be bent around the fold line 32 to rotate the proximal chambers 4 and 6 into face-to-face alignment with the middle chamber 8.

Figure 3:
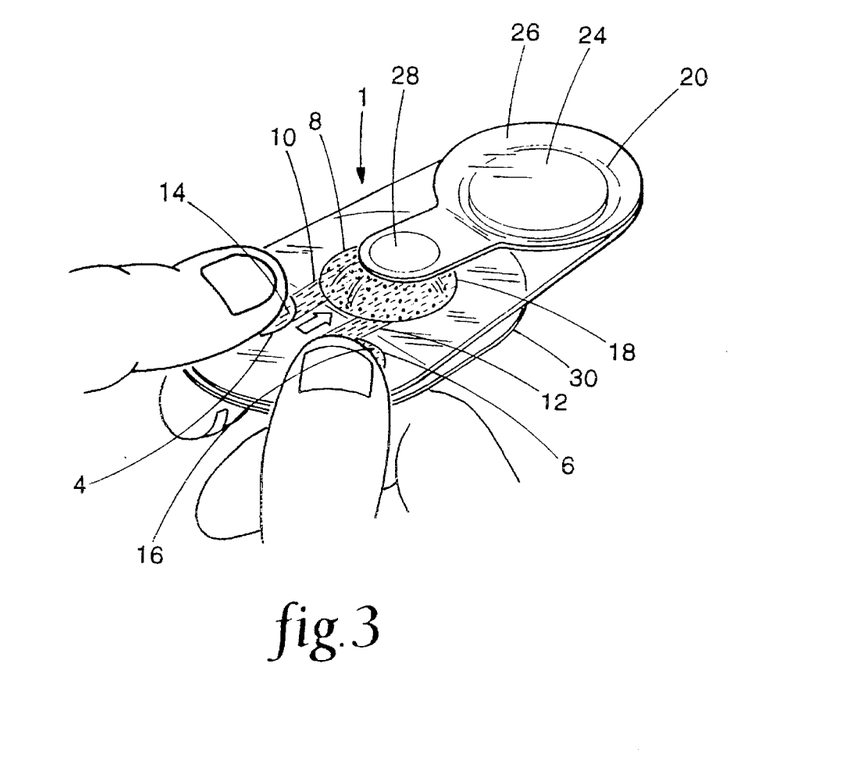
FIGS. 3–8 illustrate the steps by which the pad applicator is activated and made ready for use.
Figure 7:
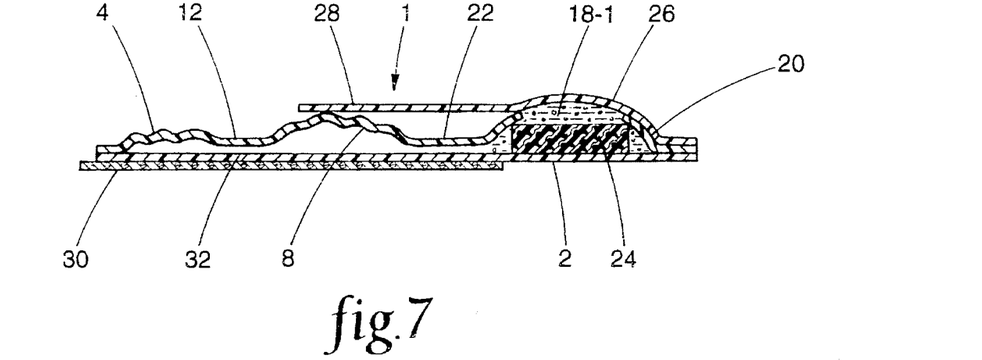
Figure 8:
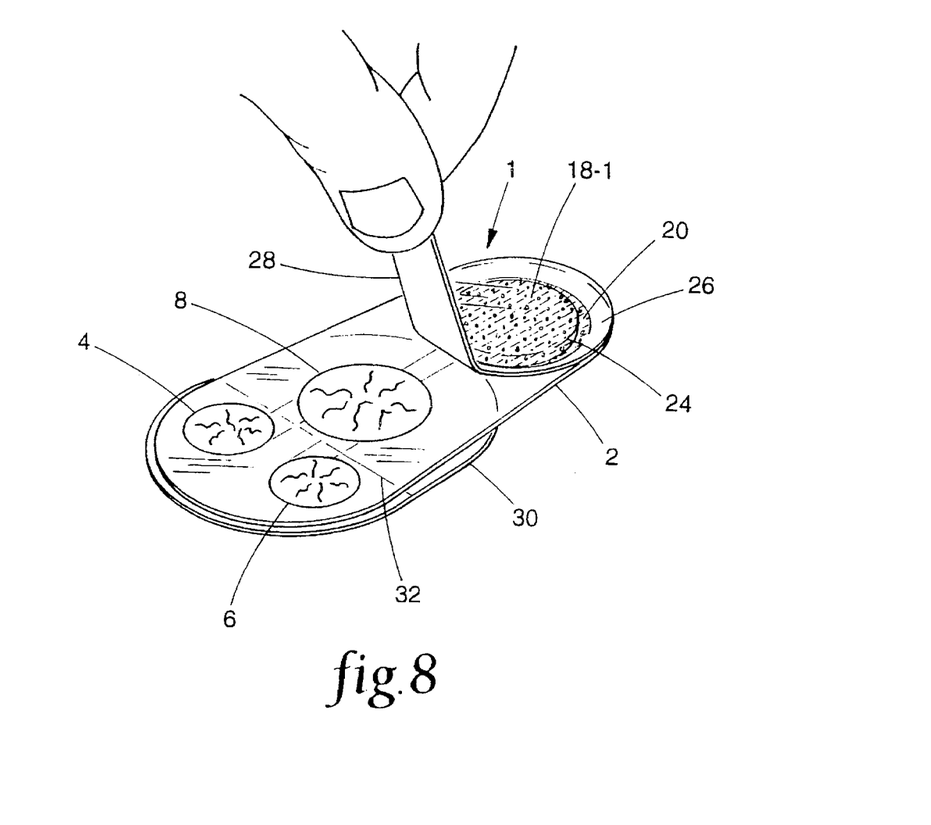
Figure 9:
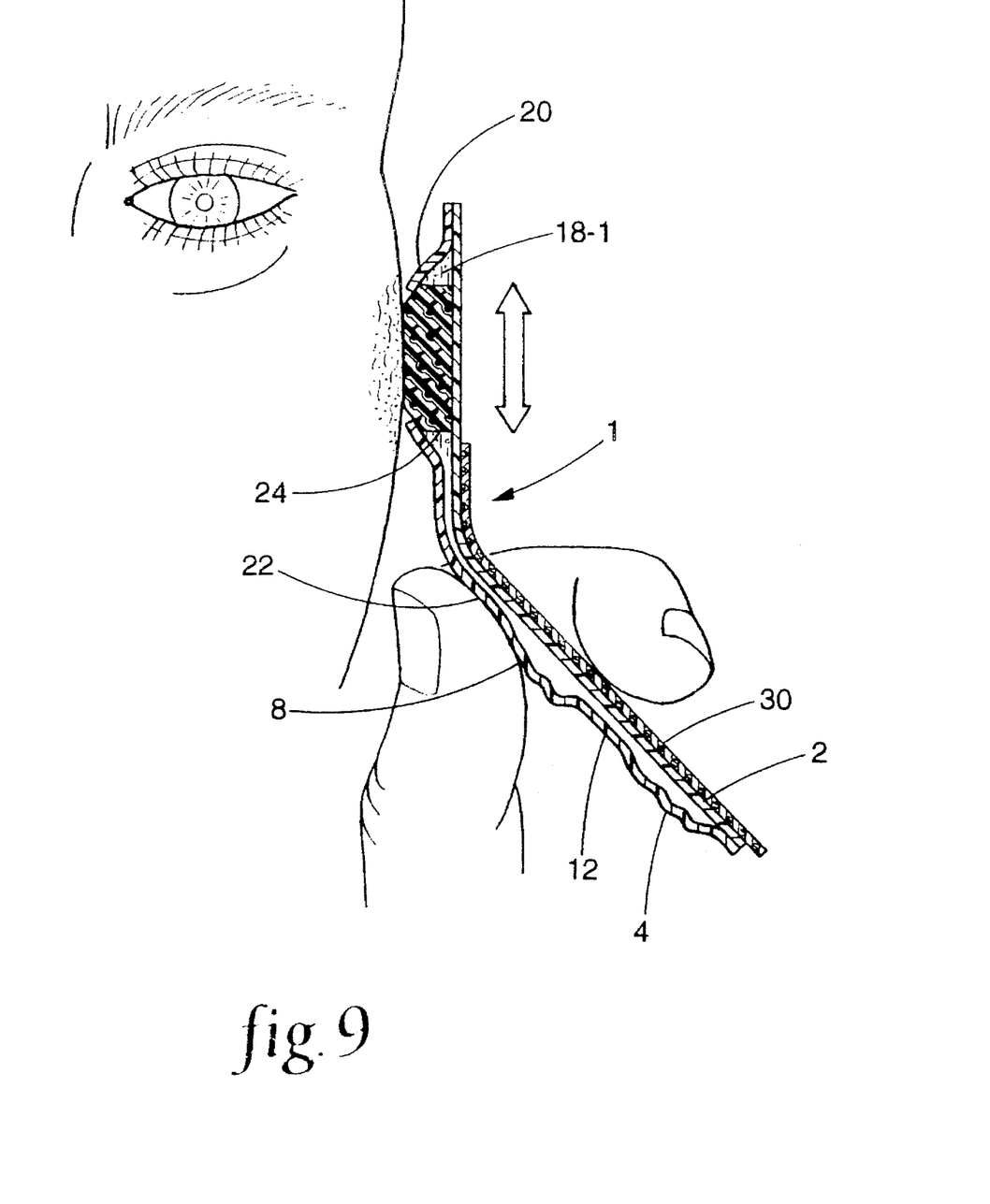
FIG. 9 shows the pad applicator moved into contact with a tissue area requiring treatment so that reconstituted liquid medication may be applied directly thereto.

The activation and use of the pad applicator 1 to apply a topical acne medication to a target site is initially described while referring to FIG. 3 of the drawings. First, with the removable cover 26 in place across the opening 21 in distal chamber 20, the user squeezes each of the bubble-shaped proximal chambers 4 and 6 (e.g. between the thumb and forefinger of his respective hands, as illustrated). The compressive squeezing forces applied to chambers 4 and 6 generate corresponding hydraulic pressures within the diluents 14 and 16. The user continues to squeeze/compress the proximal chambers 4 and 6 until the hydraulic pressures are sufficient to rupture (i.e. break) the seals established by the normally closed valves 10 and 12 (best shown in FIG. 7) so that the closures between the diluents 14 and 16 of proximal chambers 4 and 6 and the powder pharmaceutical 18 of middle chamber 8 in the packaged configuration of applicator 1 are opened. Therefore, the proximal and middle chambers 4, 6 and 8 are placed in fluid communication with one another, whereby to permit the liquid diluents 14 and 16 to be introduced, under pressure, to the powder pharmaceutical 18 by way of valves 10 and 12. Although the liquid diluents 14 and 16 have been described herein as being introduced simultaneously to the powder pharmaceutical 18, either one of the diluents 14 or 16 may be introduced to the powder 18 before the other, depending upon the chemical and/or pharmaceutical characteristics of the resultant solution.

Accordingly, the dry astringent disinfectant of powder 18 is now mixed with the liquid diluents 14 and 16 and rehydrated to form a liquid medication (designated 18-1 in FIG. 4) at the middle chamber 8. In this regard, and referring to FIG. 4 of the drawings, the user now returns the rehydrated liquid medication 18-1 from middle chamber 8 to each of the proximal chambers 4 and 6 to insure that all of the liquid diluents 14 and 16 and powder pharmaceutical 18 have been properly introduced to and mixed with one another. The foregoing is accomplished by the user squeezing the bubble-shaped middle chamber 8 (e.g. between the thumb and forefinger of one hand, as illustrated) atop the pull tab 28 of removable cover 26. The compressive force applied to chamber 8 and the corresponding hydraulic pressure generated within the rehydrated liquid medication 18-1 causes the liquid medication to be expulsed from the middle chamber 8 and delivered to the proximal chambers 4 and 6 by way of the already open valves 10 and 12.

Figure 4:
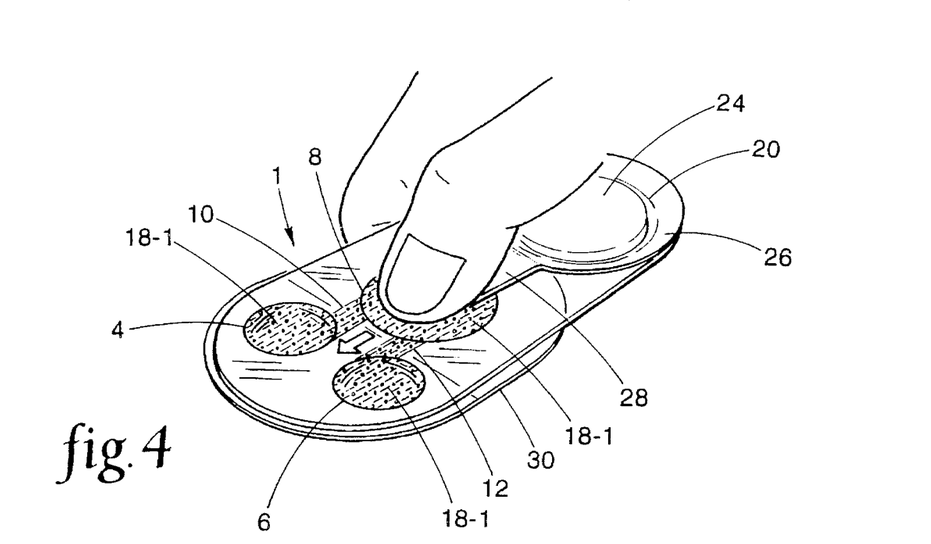

The back and forth relocations of the rehydrated liquid medication 18-1 between the middle chamber 8 and the proximal chambers 4 and 6, as illustrated in FIGS. 3 and 4, may be repeated any number of times until all of the contents of chambers 4, 6 and 8 have been completely mixed together. By virtue of the transparent nature of the material used to manufacture chambers 4, 6 and 8, the user will be able to visualize the mixing process so as to accurately determine when the entire volume of the liquid diluents has been expulsed from proximal chambers 4 and 6 and delivered to middle chamber 8 to form the rehydrated liquid medication 18-1 with the pharmaceutical composition and potency necessary to treat the user's acne.

Figure 5:
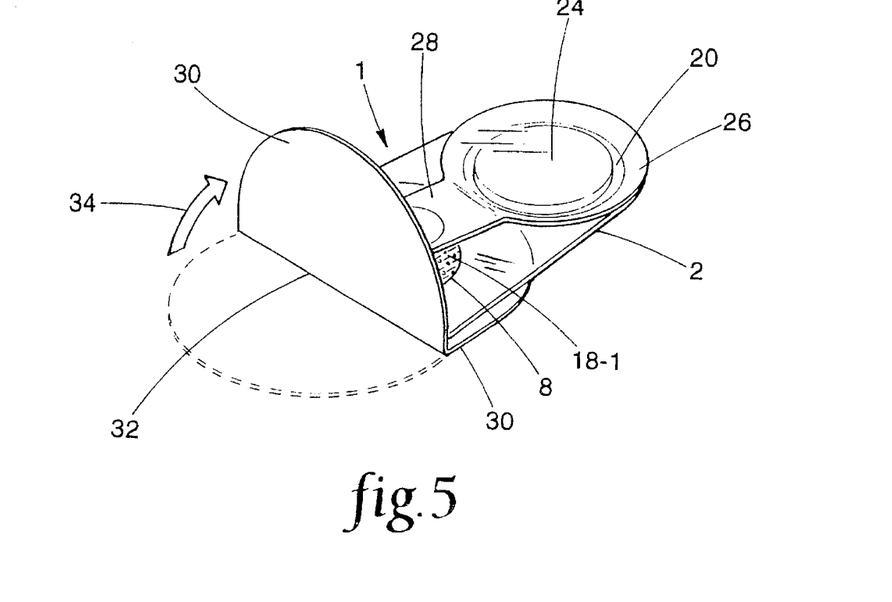
Figure 6:
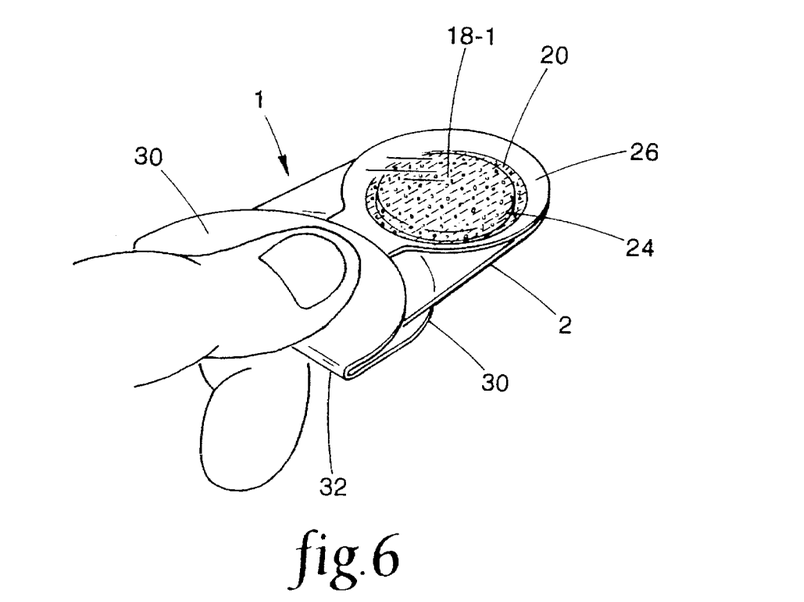

FIGS. 5 and 6 of the drawings illustrate the steps by which the rehydrated liquid medication 18-1 is expulsed from the middle chamber 8 and delivered to the distal chamber 20 to be introduced to the absorbent applicator pad 24 that is surrounded by chamber 20. To accomplish the foregoing, the user bends the relatively rigid backing 30 which, as was previously disclosed, is bonded to the bottom face of the body 2 of applicator 1 below the proximal and middle chambers 4, 6 and 8. Accordingly, the proximal end of the backing 30 is rotated relative to the distal end thereof in a clockwise direction around the fold line 32 in the direction of the reference arrow 34 of FIG. 5. A rotation of the proximal end of backing 30 causes a corresponding rotation of the proximal end of the flexible body 2 on which the proximal chambers 4 and 6 are carried. The user continues to bend the backing 30 around the fold line 32 and thereby rotate the proximal end of body 2 until the proximal chambers 4 and 6 are arranged in generally face-to-face alignment with the middle chamber 8 which contains the rehydrated liquid medication 18-1.

Figure 10:
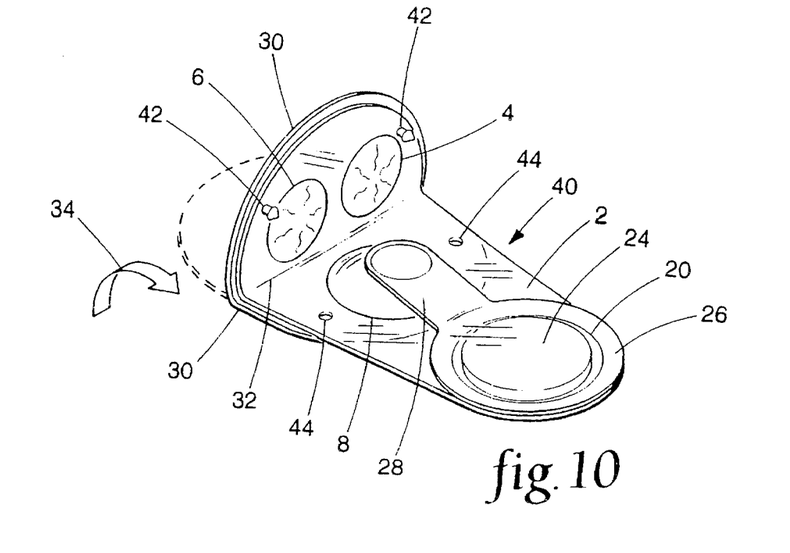
FIG. 10 is a perspective view of a multi-compartment pad applicator which includes a modification to the pad applicator of FIGS. 1–8.

FIG. 10 of the drawings shows an alternate embodiment for a single use pad applicator 40 which is similar to the applicator 1 that was described while referring to FIGS. 1–9. Therefore, like reference numerals have been used to designate the common features of both applicators 1 and 40. However, in the applicator embodiment shown in FIG. 10, one or more (e.g. two) locking tabs 42 project outwardly from the top face of the body 2 of applicator 40 adjacent respective proximal bubble-shaped chambers 4 and 6. A corresponding number of (e.g. two) receptacles or catches 44 are located in the top face of the body 2 at opposite sides of the middle bubble-shaped chamber 8. When the backing 30 is bent by the user at the lateral fold line 32, the proximal end of the flexible body 2 on which the proximal chambers 4 and 6 are carried is correspondingly rotated in a clockwise direction as represented by the reference arrow 34. The user continues to bend the backing 30 until the proximal chambers 4 and 6 are arranged in generally face-to-face alignment with the middle chamber 8, and the locking tabs 42 are received in and captured by the catches 44. The locking engagement between tabs 42 and catches 44 retains the applicator 40 in a folded configuration (similar to that illustrated in FIG. 6) to facilitate the compression of the middle chamber 8 and the expulsion therefrom of the rehydrated liquid medication 18-1 to the distal chamber 20 wherein to be absorbed by the applicator pad 24.

Figure 11:
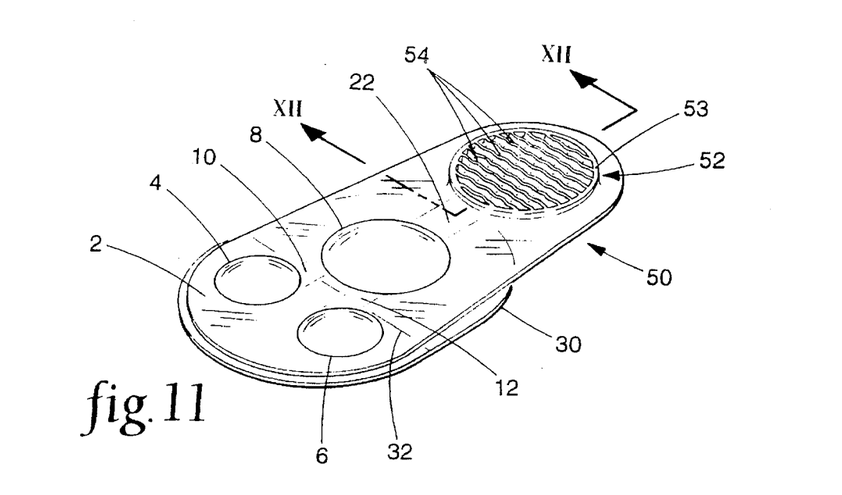
FIG. 11 is a perspective view of a multi-compartment applicator which forms a second embodiment of the present invention.
Figure 12:
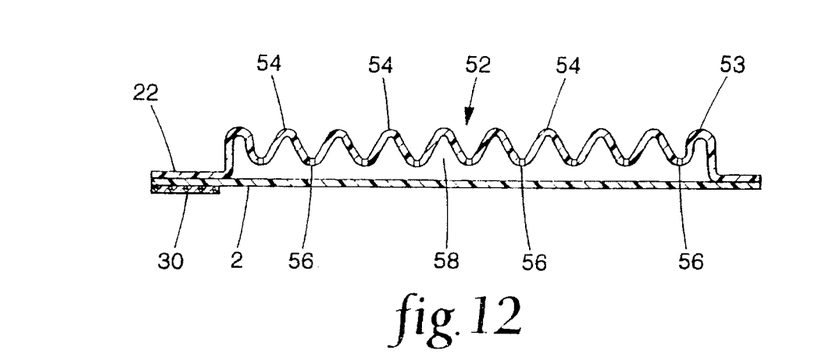
FIG. 12 is a cross-section taken along lines 12—12 of FIG. 11.

FIGS. 11 and 12 of the drawings show another embodiment for a single use applicator 50 that is also similar to the applicator 1 and for which like reference numerals have been used to designate the common features of both applicators 1 and 50. However, in the applicator embodiment shown in FIG. 11, the applicator pad (designated 24 in FIGS. 1-9) has been replaced by a channel matrix 52 that is surrounded by a distal chamber 53 and spaced slightly above the distal end of the applicator body 2 (best shown in FIG. 12). The channel matrix 52 is manufactured from a smooth, flexible material and communicates with the middle chamber 8 of applicator 50 by way of the valve 22. A removable cover (not shown) which is similar to the cover 26 that was described while referring to FIGS. 1-9 may be adhesively attached atop matrix 52 to preserve the sterility thereof in the packaged condition of applicator 50.

As is best shown in FIG. 12, the channel matrix 52 includes a plurality of parallel aligned channels 54, with each channel having a peak and a trough. A series of small holes 56 is formed through the trough in each channel 54. The holes 56 lie in fluid communication with each other and with the valve 22 at the space 58 between the applicator body 2 and the channel matrix 52. Accordingly, when the normally closed seal that has been established by valve 22 is opened (in the manner described while referring to FIGS. 6 and 7), the rehydrated liquid medication 18-1 is expulsed under pressure from middle chamber 8 for receipt by each of the channels 54 of matrix 52 via the holes 56 therethrough. The liquid medication 18-1 will be evenly distributed along the channels 54 throughout the channel matrix 52 by means of capillary action to enable a uniform application of medication from the applicator 50 to the user's tissue to be treated in the manner illustrated in FIG. 9.

Figure 13:
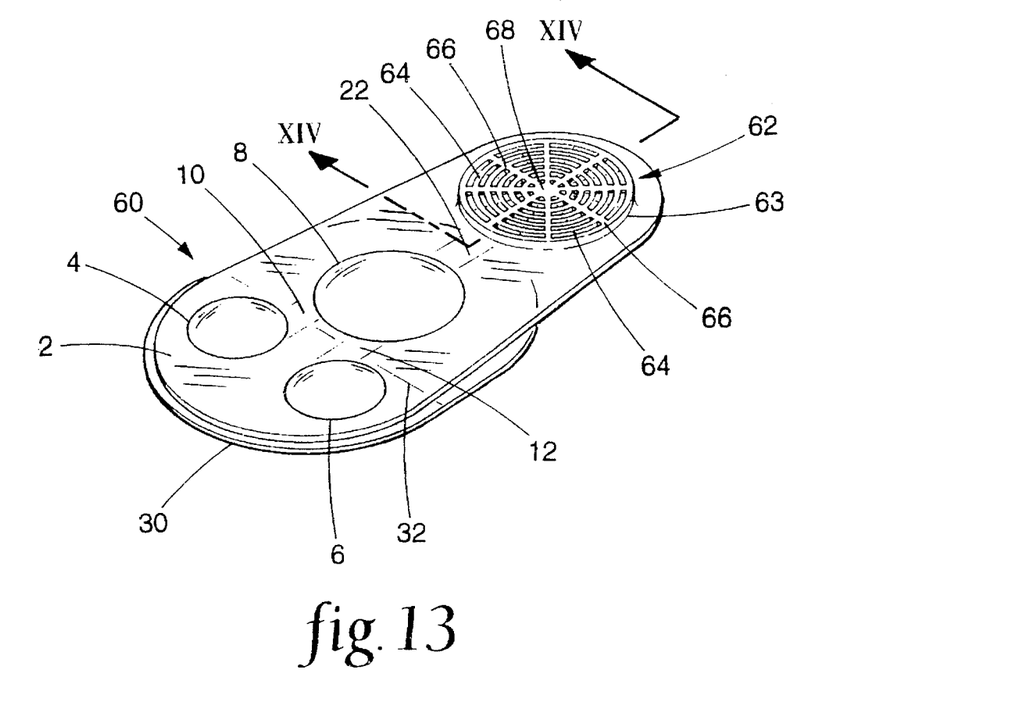
FIG. 13 is a perspective view of a multi-compartment applicator which forms a third embodiment of the present invention.
Figure 14:
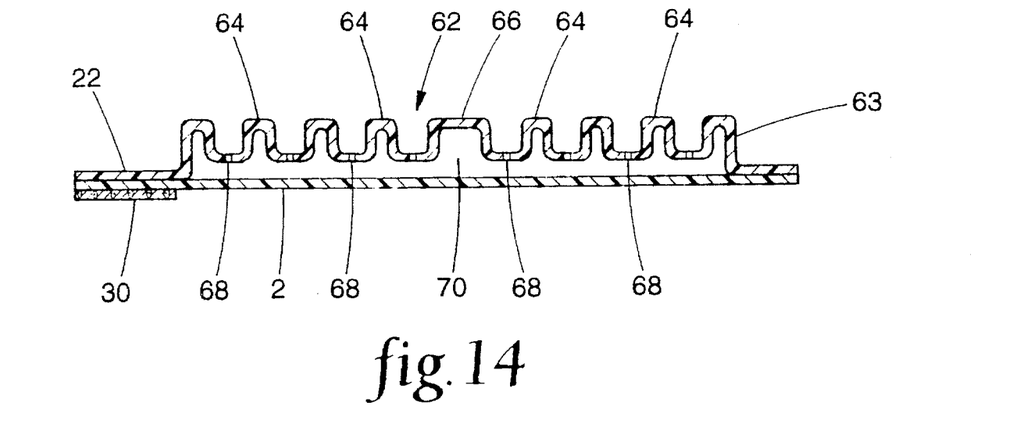
FIG. 14 is a cross-section taken along lines 14—14 of FIG. 13.

FIGS. 13 and 14 of the drawings show yet another embodiment for a single use applicator 60 which is also similar to the applicator 1 of FIGS. 1-9 and for which like reference numerals have been used to designate the common features of both applicators 1 and 60. However, the applicator pad (designated 24 in FIGS. 1-9) has now been replaced by a webbed matrix 62 that is surrounded by a distal chamber 63 and spaced slightly above the distal end of the applicator body 2 (best shown in FIG. 14). The webbed matrix 62 is manufactured from a smooth, flexible material and communicates with the middle chamber 8 of applicator 60 by way of the valve 22. A removable cover (not shown) may be adhesively attached atop matrix 62 to preserve the sterility thereof in the packaged condition of applicator 60.

As is best shown in FIG. 14, the webbed matrix 62 includes a plurality of successively larger annular channels 64 which are evenly spaced from one another around the center 68 of matrix 62. What is more, the channel matrix 62 also includes a plurality of longitudinally extending channels 66 which intersect one another at and project radially outward from the center 68 of matrix 62. Each channel 64 and 66 of the matrix 62 has a peak and a trough. A series of small holes 68 is formed through the trough in each annular channel 64. The holes 68 lie in fluid communication with each other and with the pressure activated valve 22 at the space 70 between the applicator body 2 and the webbed matrix 62.

Accordingly, when the normally closed seal that has been established by valve 22 is opened, the rehydrated liquid medication 18-1 is expulsed under pressure from middle chamber 8 for receipt by each of the annular and longitudinal channels 64 and 66 via the holes 68 through channels 64. The liquid medication 18-1 will be evenly distributed along the channels 64 and 66 throughout the webbed matrix 62 by means of capillary action to enable a uniform application of medication from the applicator 60 to the tissue to be treated in the manner illustrated in FIG. 9.

Figure 15:
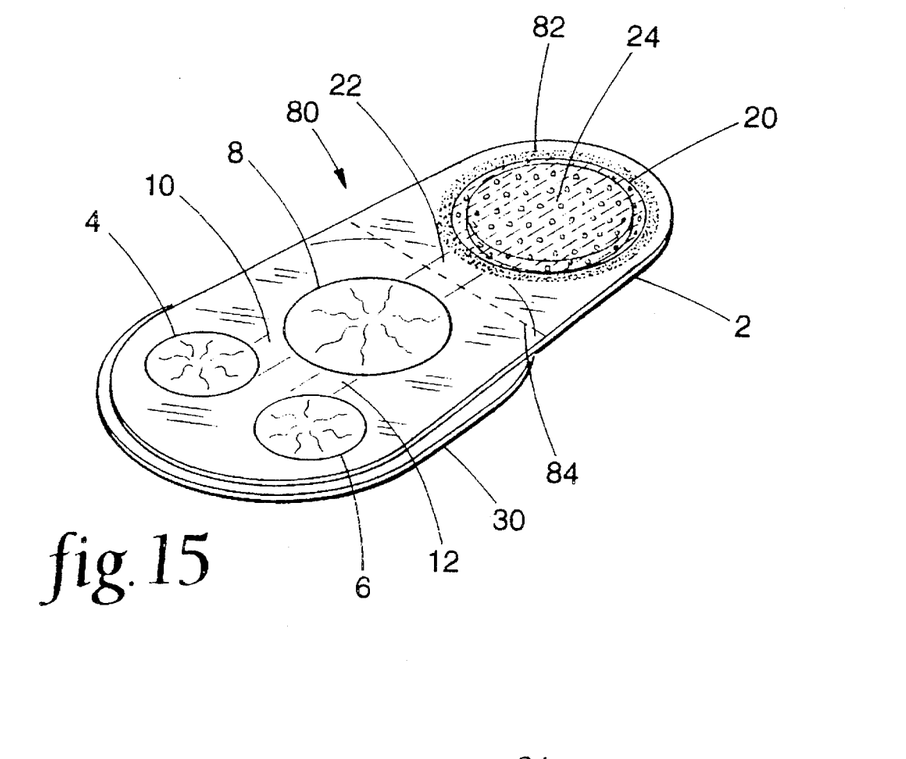
FIG. 15 is a perspective view of a multi-compartment pad applicator which includes another modification to the pad applicator of FIGS. 1–8.

It will be apparent that while the preferred embodiment of this invention has been described, various modifications may be made without departing from the true spirit and scope of the invention. For example, and as is shown in FIG. 15, by applying a suitable layer of adhesive 82 around the distal chamber 20 of a pad applicator 80 that is similar to the applicator 1 described when referring to FIGS. 1-8, the applicator 80 may be retained against the user's skin after the removable cover (designated 26 in FIG. 1) has been separated therefrom. To facilitate the foregoing, a lateral tear line 84 is formed across the body 2 of applicator 80 between the middle and distal chambers 8 and 20, whereby to separate the body 2 into proximal and distal ends.

Figure 16:
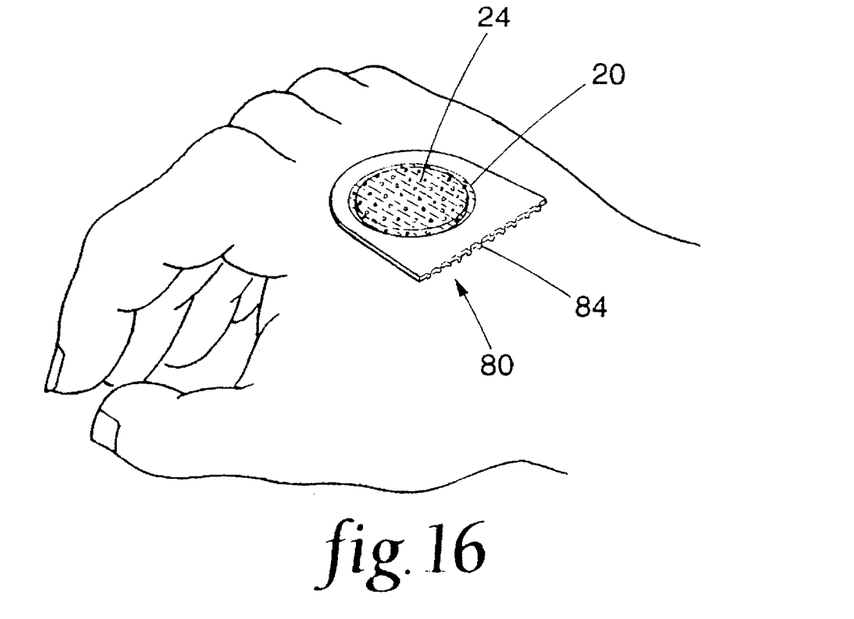
FIG. 16 shows the pad applicator of FIG. 15 attached to a tissue area to deliver a reconstituted liquid medication transdermally therethrough.

As shown in FIG. 16, the body 2 of applicator 80 is severed at the tear line 84 so that the distal end thereof can be attached to the user's skin by means of the adhesive layer 82 surrounding distal chamber 20. In this regard, the rehydrated medication that has been absorbed by the applicator pad 24 can be transdermally delivered through the user's skin by virtue of the intimate contact with pad 24 via the opening through distal chamber 20. In this embodiment, the backing 30 may be pulled off the housing 2 or eliminated from the applicator 80 altogether.

Having thus set forth the preferred embodiment of the invention, what is claimed is:

1. An applicator for applying a liquid medication to a living tissue area, said applicator comprising:

a body having a top face and a bottom face;

a first flexible chamber sealed against the top face of said body, said first flexible chamber storing therein a first liquid;

a second flexible chamber sealed against the top face of said body, said second flexible chamber storing therein a dry medication;

a first fluid path extending between said first and second flexible chambers, said first fluid path being closed to block the introduction of the first liquid stored in said first flexible chamber to said second flexible chamber, said first flexible chamber being responsive to a compressive force applied thereto to generate a corresponding hydraulic pressure within the first liquid to cause said first fluid path to open and thereby establish fluid communication between said first and second flexible chambers so that the first liquid is introduced to and mixed with the dry medication to produce the liquid medication within said second flexible chamber, said dry medication comprising a dehydrated liquid disinfectant that is rehydrated when the first liquid is introduced thereto to form the liquid medication;

a third chamber located at the top face of said body, said third chamber having an access opening formed therethrough;

fluid collection and application means surrounded by said third chamber and accessible within said third chamber by way of said access opening;

a removable cover detachably connected to said third chamber to close said access opening therethrough;

a second fluid path extending between said second flexible chamber and said third chamber, said second fluid path being closed to block the introduction of the liquid medication from said second flexible chamber to said third chamber, said second flexible chamber being responsive to a compressive force applied thereto to generate a corresponding hydraulic pressure within the liquid medication to cause said second fluid path to open and thereby establish fluid communication between said second flexible chamber and said third chamber so that the liquid medication is supplied to said fluid collection and application means; and means by which to detach said removable cover from said third chamber to open said access opening therethrough and enable said fluid collection and application means to be moved into contact with the living tissue area so that the fluid medication can be delivered to the tissue area via said access opening.

2. The applicator recited in claim 1, wherein said fluid collection and application means comprises an absorbent pad.

3. The applicator recited in claim 1, wherein said fluid collection and application means surrounded by said third chamber comprises a matrix of parallel aligned fluid channels, each of said parallel aligned fluid channels having at least one hole formed therethrough, said holes through said parallel aligned fluid channels communicating with said second flexible chamber by way of said second fluid path so that the fluid medication is supplied from said second flexible chamber to each of said parallel aligned fluid channels in said matrix via respective ones of the holes through said parallel aligned fluid channels when said second fluid path is opened and said fluid communication established between said second flexible chamber and said third chamber.

4. The applicator recited in claim 1, wherein said fluid collection and application means surrounded by said third chamber comprises a center point and a web of intersecting annular fluid channels and radial fluid channels, said annular fluid channels surrounding said center point and being spaced from one another, said radial fluid channels extending outwardly from said center point, some of said intersecting annular and radial fluid channels having respective holes formed therethrough, said holes communicating with said second flexible chamber by way of said second fluid path so that the fluid medication is supplied from said second flexible chamber to each of the intersecting annular and radial fluid channels in said web via said holes when said second fluid path is opened and said fluid communication established between said second flexible chamber and said third chamber.

5. The applicator recited in claim 1, wherein said means by which to detach said removable cover from said third chamber comprises a pull tab extending from said removable cover to a manually accessible position above the top face of said body.

6. The applicator recited in claim 1, further comprising a fourth flexible chamber sealed against the top face of said applicator body, said fourth flexible chamber storing therein a second liquid, and a third fluid path extending between said second and fourth flexible chambers, said third fluid path being closed to block the introduction of said second liquid stored in said fourth flexible chamber to said second flexible chamber, said fourth flexible chamber being responsive to a compressive force applied thereto to generate a corresponding hydraulic pressure within the second liquid to cause said third fluid path to open and thereby establish fluid communication between said second and fourth flexible chambers so that the second liquid is introduced to and mixed with the fluid medication within said second flexible chamber.

7. The applicator recited in claim 1, wherein each of said first and second flexible chambers and said third chamber is manufactured from a flexible transparent material.

8. The applicator recited in claim 1, further comprising a backing attached to the bottom face of said body so as to be located below said first and second flexible chambers at the top face of said body, said backing having proximal and distal ends and adapted to be bent so that the proximal end of said backing is rotated overtop the distal end thereof with said second flexible chamber located between said proximal and distal ends, the proximal and distal ends of said backing being squeezed together for applying the compressive force to said second flexible chamber and generating the hydraulic pressure within the liquid medication to cause said second fluid path to open and thereby establish said fluid communication between said second flexible chamber and said third chamber.

9. The applicator recited in claim 8, wherein said backing has a fold line extending laterally thereacross between said proximal and distal ends thereof, said backing being bent along said fold line.

10. The applicator recited in claim 1, further comprising a layer of adhesive disposed around said third chamber by which said third chamber is attached to the living tissue area to permit the fluid medication to be transdermally delivered through the tissue area from said fluid collection and application means via said access opening through said third chamber when said removable cover is detached from said third chamber.

11. The applicator recited in claim 10, further comprising a tear line extending laterally across said body between said second flexible chamber and said third chamber along which said body is severed to permit said third chamber to be separated from said second flexible chamber and attached to the living tissue area by means of said layer of adhesive.

12. An applicator for applying a liquid medication to a living tissue area, said applicator comprising:

a body, a first flexible chamber sealed against said body, said first flexible chamber storing therein a first liquid;

a second flexible chamber sealed against said body, said second flexible chamber storing therein a dry medication;

a first fluid path extending between said first and second flexible chambers, said first fluid path being closed to block the introduction of the first liquid stored in said first flexible chamber to said second flexible chamber, said first flexible chamber being responsive to a compressive force applied thereto to generate a corresponding hydraulic pressure within the first liquid to cause said first fluid path to open and thereby establish fluid communication between said first and second flexible chamber so that the first liquid is introduced to and mixed with the dry medication to produce the liquid medication within said second flexible chamber, said dry medication comprising a dehydrated liquid disinfectant that is rehydrated when the first liquid is introduced thereto to form the liquid medication;

a third chamber closed against said body;

fluid application means enclosed by said third chamber;

a second fluid path extending between said second flexible chamber and said third chamber, said second fluid path being closed to block the introduction of the liquid medication from said second flexible chamber to said third chamber, said second flexible chamber being responsive to a compressive force applied thereto to generate a corresponding hydraulic pressure within the liquid medication to cause said second fluid path to open and thereby establish fluid communication between said second flexible chamber and said third chamber so that the liquid medication is supplied to said fluid application means enclosed by said third chamber;

a fold line running across said body between said first and second flexible chambers, said body adapted to be bent along said fold line so that said first flexible chamber is rotated overtop and squeezed against said second flexible chamber for applying said compressive force to said second flexible chamber and generating said hydraulic pressure within the liquid medication to cause said second .fluid path to open so that the liquid medication is supplied from said second flexible chamber to said fluid application means enclosed by said third chamber; and means by which to open said third chamber to permit said fluid application means to be moved into contact with the living tissue area so that the fluid medication can be delivered to the tissue.

13. The applicator recited in claim 12, further comprising an access opening formed through said third chamber, a removable cover detachably connected to said third chamber to close said access opening, and means by which to detach said removable cover from said third chamber to open said access opening and thereby permit said fluid application means to be moved into contact with the living tissue area.

14. The applicator recited in claim 13, wherein said means by which to detach said removable cover from said third chamber comprises a pull tab extending from said removable cover to a manually accessible position above said body.

15. The applicator recited in claim 13, further comprising a layer of adhesive disposed on said body around said third chamber by which said third chamber is attached to the living tissue area to permit the fluid medication to be transdermally delivered through the tissue area from said fluid application means via said access opening through said third chamber when said removable cover is detached from said third chamber.

16. The applicator recited in claim 12, wherein each of said first and second flexible chambers and said third chamber is manufactured from a flexible transparent material.

17. The applicator recited in claim 12, further comprising a fourth flexible chamber sealed against said applicator body, said fourth flexible chamber storing therein a second liquid, and a third fluid path extending between said second and fourth flexible chambers, said third fluid path being closed to block the introduction of the second liquid stored in said fourth flexible chamber to said second flexible chamber, said fourth flexible chamber being responsive to a compressive force applied thereto to generate a corresponding hydraulic pressure within the second liquid to cause said third fluid path to open and thereby establish fluid communication between said second and fourth flexible chambers so that the second liquid is introduced to and mixed with the fluid medication within said second flexible chamber.

18. The applicator recited in claim 12, wherein said fluid application means enclosed by said third chamber comprises a matrix of parallel aligned fluid channels, each of said parallel aligned fluid channels having at least one hole formed therethrough, said holes through said parallel aligned fluid channels communicating with said second flexible chamber by way of said second fluid path so that the fluid medication is supplied from said second flexible chamber to each of said parallel aligned fluid channels in said matrix via respective ones of the holes through said parallel aligned fluid channels when said second fluid path is opened and said fluid communication established between said second flexible chamber and said third chamber.

19. The applicator recited in claim 12, wherein said fluid application means enclosed by said third chamber comprises a center point and a web of intersecting annular fluid channels and radial fluid channels, said annular fluid channels surrounding said center point and being spaced from one another, said radial fluid channels extending outwardly from said center point, some of said intersecting annular and radial fluid channels having respective holes formed therethrough, said holes communicating with said second flexible chamber by way of said second fluid path so that the fluid medication is supplied from said second flexible chamber to each of the intersecting annular and radial fluid channels in said web via said holes when said second fluid path is opened and said fluid communication established between said second flexible chamber and said third chamber.

20. The applicator recited in claim 12, wherein said fluid application means enclosed by said third chamber comprises an absorbent pad.

* * * * *